US010412937B2

(12) United States Patent
Tokle et al.

(10) Patent No.: US 10,412,937 B2
(45) Date of Patent: Sep. 17, 2019

(54) MARINE MATERIAL DERIVED FROM EARLY DEVELOPMENTAL STAGES OF BARNACLES

(71) Applicant: PLANKTONIC AS, Trondheim (NO)

(72) Inventors: Nils Egil Tokle, Trondheim (NO); Havard Johan Aakeroy, Trondheim (NO)

(73) Assignee: PLANKTONIC AS, Heroy (NO)

( * ) Notice: Subject to any disclaimer, the term of this patent is extended or adjusted under 35 U.S.C. 154(b) by 0 days.

(21) Appl. No.: 16/219,112

(22) Filed: Dec. 13, 2018

(65) Prior Publication Data

US 2019/0166807 A1 Jun. 6, 2019

Related U.S. Application Data

(62) Division of application No. 14/441,328, filed as application No. PCT/NO2013/050192 on Nov. 8, 2013, now abandoned.

(30) Foreign Application Priority Data

Nov. 8, 2012 (NO) .................................. 20121315

(51) Int. Cl.
*A61K 36/00* (2006.01)
*A01K 61/59* (2017.01)
*A23K 50/80* (2016.01)
*A23L 17/00* (2016.01)
*A61K 35/612* (2015.01)

(52) U.S. Cl.
CPC .............. *A01K 61/59* (2017.01); *A23K 50/80* (2016.05); *A23L 17/00* (2016.08); *A61K 35/612* (2013.01); *A23V 2002/00* (2013.01); *Y02A 40/824* (2018.01)

(58) Field of Classification Search
CPC .................................................... A61K 36/00
USPC ....................................................... 424/725
See application file for complete search history.

(56) References Cited

U.S. PATENT DOCUMENTS

2011/0200707 A1 8/2011 Kortes
2013/0280379 A1 10/2013 Kortes

FOREIGN PATENT DOCUMENTS

| CN | 1 593 464 | 3/2005 |
| CN | 101578967 A | 11/2009 |
| NO | 20023374 | 8/2002 |
| WO | 93/11675 | 6/1993 |
| WO | 01/50880 | 7/2001 |
| WO | 2010/046313 | 4/2010 |

OTHER PUBLICATIONS

*Barnacle Biology*, CRC Press, A.J. Southward (Editor), p. 241, 1987.
Matsumura et al., "Immunological Studies on the Settlement-Inducing Protein Complex (SIPC) of the Barnacle *Balanus amphitrite* and its Possible Involvement in Larva-Larva Interactions," *Proc. R. Soc. Lond.* B, vol. 265, pp. 1825-1830, 1998.
Australian Office Action issued in AU Patent Appl. No. 2013341870, dated Jun. 29, 2016.
Lopez et al., "Potency of Barnacle in Aquaculture Industry", In: *Aquaculture*, Chapter 15, ISBN 978-953-307-974-5, InTech, pp. 295-316, 2012.
Barnes et al., "Phototaxis in Stage I Nauplius Larvae of Two Cirripedes", *J. Exp. Mar. Biol. Ecol.*, vol. 10, No. 3, pp. 267-273, 1972.
Daniel et al., "Barnacle Larvae (*Balanus* spp.) as a Potential Diet for Juvenile Lobsters (*Homarus americanus*)", *Aquaculture*, vol. 46, pp. 67-70, 1985.
Wullur et al., "The Minute Monogonont Rotifer *Proales similis* de Beauchamp: Culture and Feeding to Small Mouth Marine Fish Larvae", *Aquaculture*, vol. 293, pp. 62-67, 2009.
Homan et al., "Rapid Separation and Quantitation of Combined Neutral and Polar Lipid Classes by High-Performance Liquid Chromatography and Evaporative Light-Scattering Mass Detection",*J. Chromatogr. B.*, vol. 708, pp. 21-26, 1998.
Moreau, "The Analysis of Lipids via HPLC with a Charged Aerosol Detector", *Lipids*, vol. 41, No. 7, pp. 727-734, 2006.
Bligh et al., "A Rapid Method of Total Lipid Extraction and Purification", *Can. J. Biochem. Physiol.*, vol. 37, No. 8, pp. 911-917, 1959.
Rainbow et al., The Functional Morphology and Development of the Alimentary Tract of Larval and Juvenile Barnacles (Cirripedia: Thoracica), *Marine Biology*, vol. 42, pp. 337-349, 1977.
Lee et al., "Lipid Changes During Life Cycle of Marine Copepod, *Euchaeta japonica*Marukawa", *Lipids*, vol. 9, No. 11, pp. 891-898, Nov. 1, 1974.
Lopez et al., "Barnacle Culture: Background, Potential and Challenges", *Aquaculture Research*, vol. 41, pp. e367-e375, 2010.
International Search Report for PCT/NO2013/050192, dated Mar. 12, 2014.
Written Opinion of the ISA for PCT/NO2013/050192, dated May 12, 2015.
Norwegian Search Report for Norwegian Patent Application No. 20121315, dated Jun. 7, 2013.
Molares et al., Marine Biology, 1994, 120:261-264.
Collis et al., Comp. Biochem. Physiol., 1995, vol. 112, No. 2, pp. 327-332.
Achituv et al., J. exp. Mar. Biol. Ecol., 1980, vol. 42, pp. 1-12.

*Primary Examiner* — Michael V Meller
(74) *Attorney, Agent, or Firm* — Greenblum & Bernstein, P.L.C.

(57) ABSTRACT

The present invention relates to a nutritional product comprising a biological material derived from eggs and/or nauplii of stage I of a barnacle and its uses. The invention, especially discloses a feed for early live stages of aquatic animals such as fish or crustaceans comprising isolated eggs and/or nauplii of stage I of a barnacle or a material derived thereof. Methods for harvesting, isolating and preservation of the biological barnacle material are also disclosed.

7 Claims, 1 Drawing Sheet

MARINE MATERIAL DERIVED FROM EARLY DEVELOPMENTAL STAGES OF BARNACLES

The present application is a Divisional of U.S. application Ser. No. 14/441,328, which is a National stage of International Patent Application No. PCT/NO2013/050192 filed Nov. 8, 2013, which claims priority to Norway Application No. 20121315 filed Nov. 8, 2012. The disclosures of U.S. application Ser. No. 14/441,328 and International Patent Application No. PCT/NO2013/050192 are incorporated by reference herein in their entireties.

FIELD OF THE INVENTION

The present invention relates to a nutritional product and its use. The present invention also relates to the use of eggs and nauplius stage I of a barnacle. Furthermore, the present invention relates to methods for harvesting and isolating of eggs and/or nauplii of stage I from a sessile, mature barnacle attached to a surface. Finally, the present invention relates to methods for preserving the nutritional product and for preserving of eggs and nauplii of stage I of a barnacle as well as to a composition.

BACKGROUND TO THE INVENTION

Feed containing a high content of marine unsaturated fatty acids has proven to be beneficial for the normal development and nutritional quality of many cultured aquatic species used in human consumption. Today, the cultivation of many marine fish and crustacean species largely depends on feeding of living prey during their first developmental stages.

Artificial diets such as micro diets are in general little successful in first feeding of the precocious marine fish and crustacean larvae. Several reason have been suggested which could cause the failure of micro diets in first feeding of marine larvae. Apart from reduced feeding rates due to a lower acceptance, an insufficient nutritional quality of the diet not covering the requirements of the larvae and/or the high organic load causing microbial problems and accompanied reduced water quality have been suggested as causative for the failure of artificial diets. Other suggested reasons are a reduced digestibility of the diets, which has been suggested to be a result of a possible lack of enzymes in the micro diets. The later reason is based on the fact that marine fish larvae lack a stomach in the larval phase and thus an efficient peptic digestion of feed. It has been suggested that the enzymes, as naturally included in the live feed prey, may be necessary for an efficient digestion of feed in the early stages or as a factor stimulating/activating the endogenous excretion and synthesis of larval digestive enzymes. Besides other factors, inadequate feeding during the first life stages of marine fish larvae such as the Atlantic cod, Atlantic halibut and turbot not only result in reduced growth, but also in high mortalities, decreased larval quality and mal pigmentations and mal developments.

In aquaculture, the most common prey organisms used to feed marine fish larvae are belonging to the group of rotifers especially some species belonging to the family of Brachionidae and to the brine shrimp Artemia spec. However, the nutritional composition of both, rotifers, and Artemia is naturally poor and not suitable for feeding of marine fish larvae. Therefore, these organisms have to be cultivated in intensive cultures and must be enriched with marine lipids, especially omega-3 fatty acids to improve their nutritional quality as prey organisms for marine fish larvae. This makes the cultivation of these prey organisms laborious and expensive. But in spite of the mentioned enrichment, both Artemia and rotifers are still not found nutritionally optimal for many larval species. This is reflected in mortality rates, growth rates, mal pigmentations and mal developments. Thus, there is a clear need for more optimal replacement diets for first feeding larvae as well as for early life stages of many cultivated crustaceans which e.g. use enriched Artemia as diet.

Furthermore, there is a large need for marine derived biological material rich in omega-3 fatty acids which is suitable for use in animal and human consumption. The increasing awareness of the beneficial effects of omega-3 fatty acids in sectors such as human consumption, pharmaceutical compositions and for health purposes in humans and other animals than fish further increases the quantitative demand for these fatty acids. Today, the main source for marine biological raw material are fish oil and fish meals. However, due to over-fishing accompanied by a globally increasing demand, there is an increasing need for new, unexploited biological marine sources to cover the demand.

Barnacles are an industrially hardly exploited organism. Barnacles are a type of arthropod belonging to the infraclass Cirripedia in the subphylum Crustacea. Barnacles are exclusively marine, and tend to live in shallow and tidal waters. They are sessile (non-motile) suspension feeders. Around 1,220 barnacle species are currently known. Two major types of barnacles are found in the oceans, the goose barnacles and the acorn barnacles.

Barnacles incubate their eggs in the body cavity, where they further develop to the one-eyed nauplius stage I. Nauplius I are released from the parent to the water column where they develop to nauplius stage II after a short time, typically within one day. Nauplius stage II have a fee-swimming, planktonic life lasting several weeks during which the nauplius II initiates an active feeding behavior. The free-living planktonic nauplius stages develop different appendages such as frontal horns which can already be observed in nauplius stage II. Several nauplii stages are then completed as plankton (nauplius larvae II to nauplius larvae VI), until converting into competent cyprid larvae. Cyprid is the final planktonic stage, which settles to a substrate, and thereafter undergoes a metamorphosis to the form of an adult specimen.

As barnacles attach themselves to man-made structures, especially to ships, as well as to biological material such as the shells of mussels for consumption, they are mainly and almost exclusively recognized as fouling organisms, their presence having negative economic consequences. Studies on barnacle so far have therefore mainly focused on factors influencing the attachment of barnacles as well as methods of elimination of barnacles from surfaces. Some mature barnacles are considered edible by humans, especially goose barnacles and giant barnacles. Goose barnacles are for example cultivated for this purpose.

Barnacles have been cultivated for commercial applications and research purposes with the aim to harvest them in their sessile stage. Lopez et al. 2012 describes the cultivation of spat barnacles to adult species for human consumption (López, D. A.; López B. A., Pham, C. K., Isidro, E. J. 2012. Potency of barnacle in aquaculture industry. In: Aquaculture, Editor: Muchlisin, Z., ISBN 978-953-307-374-5, Intech.).

Barnacles are also harvested from the wild by either collecting them in the planktonic stage or by removal of the sessile organisms.

Free-swimming planktonic barnacle larvae have been filtrated from the water and tested as a diet for juvenile lobster (Daniel, P. C., Bayer, R. C., Chapman, S. 1985. Barnacle larvae (*Balanus* spp.) as a potential diet for juvenile lobster (*Homarus americanus*). Aquaculture 46, p 67-70). Tests carried out with planktonic barnacles nauplii as live feed for fish larvae are also mentioned (see Wullur S., Sakakura, Y., Hagiwara, A. 2009. The minute monogonont rotifer Proales similis de Beauchamp: Culture and feeding to small mouth marine fish larvae. Aquaculture 293, p. 67), but they were not considered as optimal for this purpose.

Another application of barnacle raw material is described in CN1593464, which discloses an anti-inflammation and pain easing health product which is extracted from a barnacle raw material.

The objective technical problem to be solved by the present invention is to provide a new biological resource for nutritional products such as feed as well as methods for the exploitation of a new marine biological resource which can be industrially applied for different purposes. Thus, the present invention aims at providing a new biological resource for marine based products and a method for exploiting and producing it.

A further aim is to provide the new biological resource for the marine based product in a particular pure form without being mixed with other biological material.

In particular, the present invention has the objective to provide an optimized diet useful for feeding of aquatic animals such as fish and crustaceans, especially in their early life stages as well as for ornamental aquatic species.

SUMMARY OF THE INVENTION

According to a first aspect, the present invention relates a nutritional product which is wherein the product comprises biological material derived from eggs and/or nauplii of stage I of a barnacle.

The product can further comprise nauplius stage II of a barnacle. Preferably, at least 70% of the comprised material in the nutritional product are nauplius stage I, more preferred at least 80%, even more preferred at least 90%, even more preferred at least 95%, and most preferred at least 99% of the material in relation to the total wet weight or total number of organisms. Preferably, the nutritional product has a content of eggs, which is less than 30%, more preferred less than 20%, even more preferred less than 10% and most preferred less than 5% in relation to the wet weight or number of organisms comprised in the product. Another preferred embodiment according to the present invention has a content of barnacle nauplius stage II, which is less than 50%, more preferred 20%, even more preferred less than 10% and most preferred less than 5% in relation to the wet weight or number of organisms comprised in the product.

It is also preferred that the barnacle material comprised in the product only comprises nauplius stage I, or only comprises eggs, or only comprises a combination of nauplius stage I with eggs and/or nauplius stage II of a barnacle.

Furthermore it is preferred that the nutritional product does not comprise living developmental stages of barnacles.

The product can be a feed product for an animal, preferably for an aquatic animal, more preferably for a farmed aquatic animal selected from fish and crustacean, for an ornamental vertebrate or for ornamental invertebrate and most preferred for early live stages of a fish or of a crustacean, which is preferably a species selected from a marine fish larvae, a crab, a shrimp, a prawn and a lobster.

In another preferred embodiment, said product comprises or consists of an oil derived from eggs and/or nauplius stage I or a combination of eggs and/or nauplius stage I with nauplius stage II of a barnacle.

A second aspect according to the present invention relates to a use of a product according to any of the preceding paragraphs for feeding of a farmed aquatic animal, an ornamental vertebrate or an ornamental invertebrate, either directly or comprised in a feed with other ingredients.

A third aspect of the present invention relates to a use of eggs and/or nauplius stage I of a barnacle for animal and human consumption, as a feed supplement, a health product and/or a functional feed.

A fourth aspect of the present invention relates to a method for harvesting and isolating of eggs and/or nauplii of stage I from a sessile, mature barnacle attached to a surface wherein the eggs and/or nauplii of stage I are removed directly from the sessile barnacle by washing said eggs and nauplii stage I out of the sessile mature barnacles by water jetting, and thereafter collecting.

Another aspect of the present invention relates to a method for harvesting and isolating of eggs and/or nauplii of stage I from a sessile, mature barnacle attached to a surface for use in a product according to claim 1 wherein the eggs and/or nauplii of stage I are:

removed from the sessile barnacle after said barnacle has been detached from said surface by mechanical forces and/or water jetting, and the removed mature barnacles are collected together with the eggs and/or nauplii of stage I, and optionally releasing eggs and/or nauplii of stage I still attached to the barnacle after said detachment by use of mechanical forces and/or washing; and separating the eggs and/or nauplii from the mature barnacles by a separation method.

The obtained eggs and nauplii stage I can be fractionated after release from the mature barnacles in different size fractions either by a mechanical separation method, preferably selected from sieving, filtration and/or centrifugation, or by application of light causing a phototactic response of the nauplius larvae.

The applied method for harvesting can comprise an additional step for increasing the content of nauplius stage I in the material after harvesting by incubating the isolated living eggs and/or nauplius stage I still comprised in the egg membrane for a defined period of time in sea water to hatch/release nauplius I which are still situated in the egg membrane to free swimming nauplius I.

Preferably, the incubation temperature is between 5 and 10° C., more preferred about 8° C. and the incubation time between 5 and 12 hours, preferably about 10 hours.

In another aspect, the present invention relates to a method for preserving eggs and/or nauplii of stage I of a barnacle wherein the barnacle material is preserved by a heat treatment which is chosen from heating to a temperature between 55° C. and less than 70° C., pasteurization by heating to at least 70° C., preferably above 75° C. and sterilization above 100° C. and optionally stored.

The present invention also relates to a method for preserving of a barnacle material for a product according to of the preceding paragraphs, wherein the comprised harvested nauplii and/or eggs are treated by one or several of the methods selected from cooling below the animals freezing point, heat treatment, drying, freeze drying, storage in a modified atmosphere, and addition of preserving chemicals.

Preferably, the material is stored below the freezing point, preferably at −18° C. or lower, more preferably at −80° C. or lower with or without previous preservation.

It is also preferred that the material is stored in a modified atmosphere, preferably in nitrogen gas, more preferred storage in a modified atmosphere and at a temperature below 4° C. with or without previous preservation.

The present invention also relates to a composition comprising eggs and/or nauplius stage I of barnacles or a material derived thereof for use in a prophylactic or medical treatment. Preferably said composition is used to improve growth, survival and/or malpigmentation of an animal, preferably of an aquatic animal.

Preferred embodiments are also defined in the dependent claims.

A particularly preferred species according to the present invention is the acorn barnacle *Semibalanus balanoides*. It is known that adult *S. balanoides* grow up to 15 millimeters in diameter, living attached to rocks and other solid substrates. *S. balanoides* is found in the intertidal zone in the world's northern oceans. Its distribution is limited in the north by the extent of the pack-ice and in the south by increasing temperature which prevents maturation of gametes. *S. balanoides*, as the majority of other barnacles, is hermaphroditic, but cannot fertilize itself. Up to 10,000 eggs may be produced per individual, and they are stored in sacs within the shell cavity. While the eggs are developing, the adult barnacle does not moult. The eggs hatch into nauplius larvae, which have three pairs of legs, one pair of antennae and a single eye and are released as nauplius developmental stage I whereafter they quickly developed to nauplius stage II to coincide with the spring algal bloom.

Other barnacles species useful according to the present invention are any suitable barnacles chosen from the infraclass cirripedia. Without being restricted to the following examples, of particular interest are species selected from the genuses *Semibalanus*, *Balanus*, *Austrominius*, *Amphibalanus*, *Verruca*, *Chirona*, *Notoch-thamalus*, *Jehlius*, *Chthalamus* and *Belanus*.

It will be appreciated that features of the invention described in the foregoing can be combined in any combination without departing from the scope of the invention.

DETAILED DESCRIPTION OF THE INVENTION

Embodiments of the present invention will now be described in detail and further illustrated and supported by the way of examples with reference to the following diagram, wherein.

Barnacles used in the following tests and experiments according to the present invention were of the species *Semibalanus balanoides* and were all harvested in Norway. *S. balanoides* is a common and widespread acorn species, which is common on rocks and other substrates in the intertidal zone of north-western Europe and both coasts of North America and can therefor also typically be harvested from other locations outside Norway.

If not disclosed otherwise, the following method was used to prepare the barnacle product used in the following described experiments: The organisms were caught from the wild in Norwegian coastal waters by the method of mechanically removing parental animals from shore rock and thereafter removing the nauplii from the parental animals by mechanical crushing and sieving on 1000, 500 and 100 μm stainless steel filter, where the nauplii I were harvested between the 100-500 μm filter. The nauplii were directly transferred to 70° C. seawater for a minimum of 15 minutes, and thereafter packed in retortable aluminium laminated pouches with $N_2$ gas and sterilized in a retort at 112 C and 1.7 bar for 40 minutes.

I. Harvesting of Barnacle Eggs, Nauplii Stage I from Sessile Barnacles:

Mature adult barnacles are sessile and typically attached to different substrates. As the eggs and nauplii stage I are brood in the sessile barnacle and thereafter released, a preferred harvesting method for these life stages includes to remove the sessile barnacle from the substrates where it is attached to together with the eggs and nauplius larvae I. Such substrates can typically be surfaces of materials such as stones, wood, concrete, and plastic. The eggs and nauplii stage I can be harvested and isolated from wild or artificial cultures of barnacles.

Sessile barnacles are typically removed by mechanical forces such as scraping, breaking, crushing, use of pressure etc. Another particular preferred method is water-jetting using high pressured water.

The removed biological material comprising eggs and nauplii stage I are collected for further processing. If the adult barnacles are detached from the surface together with the eggs and nauplii stage I, they are collected together with the early life stages and preferably separated from each other in an additionally performed step.

If the eggs and nauplii stage I are not released from the adult organisms after detaching of the sessile organisms from the surface, an additional separation of the organisms is performed. Typically mechanical forces such as breaking and crushing are used. It is an advantage that the nauplii or eggs are not destroyed or as little as possible. An alternative method includes washing with high pressured water (water jetting) to release the eggs and nauplii stage I from the adult barnacle.

The adult animals are thereafter separated from the eggs and nauplii stage I using a suitable separation method. It is preferred to use a mechanical separation method such as sieving, filtration and/or centrifugation.

Sieving can for example be carried out by using filter with a mesh size of 1000, 500 and 100 μm (e.g. a stainless steel filter), where the nauplii I are harvested between the 100-500 μm filter.

An alternative harvesting method is a method where the mature barnacles comprising the eggs, nauplii stages I are not removed from their substrates. In this methods the eggs and nauplii stage I are washed out of the mature barnacles by water jetting without detaching the adult organisms from the surface. The eggs and nauplii of stage I are thereafter collected for further processing. Optionally, the isolated eggs and nauplii of stage I are separated in different size fractions by a mechanical separation method, preferably selected from sieving, filtration and/or centrifugation.

Thus, the following method steps for harvesting and isolating of eggs and nauplii of stage I from a sessile barnacle are typically performed in accordance with the present invention:

i.) removing the sessile mature barnacle from the surface where it is attached to by mechanical forces and/or water jetting;

ii.) collecting of the removed mature barnacles together with the eggs and nauplii of stage I for further processing;

iii.) if necessary release of the eggs and nauplii of stage I from the mature barnacle by use of mechanical forces and/or washing; and iv.) separating of the egg/nauplii material from the mature barnacles by a mechanical separation method, preferably selected from sieving, filtration and centrifugation.

Optionally and in addition a separation of the isolated eggs and nauplii of stage I in different size fractions is carried out by a mechanical separation method, preferably selected from sieving, filtration and/or centrifugation, either simultaneously with step iv.) or thereafter.

Alternatively, as method for harvesting and isolating of eggs and nauplii of stage I from a sessile barnacle the following steps are carried out:

i.) washing eggs and nauplii stage I out of the adult mature barnacles by water jetting, ii.) collecting of the eggs and nauplii of stage I for further processing;

iii.) optionally separating of the isolated eggs and nauplii of stage I in different size fractions by a mechanical separation method, preferably selected from sieving, filtration and/or centrifugation.

The early life stages harvested from parent barnacles consist to a vast majority of nauplius stage I. Typically, only small amounts of eggs are found and depending on the season eggs are in some cases hardly found. In this way the harvested early life stages substantially only comprise nauplius stage I right after harvesting.

Frequently, some minor amounts of nauplius stage II are observed in the isolated material. This is probably caused by that some of the nauplius larvae in stage I develop to the stage II during harvesting. The amount/number of stage II nauplius larvae depends on the time used for harvesting and from harvesting until the samples are preserved. If preservation is carried out directly or within a short time span after harvesting, nauplius stage II are not found or their presence is such low that it is neglectable. A preferred product according to the present invention has a high amount of nauplius larvae stage I and it is therefore preferred that the time span between harvesting and preservation is short in order to stop the further development of the nauplius stage I to nauplius stage II. Most preferred is a direct preservation after harvest to stop the further development as well as to maintain the most optimal quality of the harvested material.

A preferred nutritional product according to the present invention has an initial composition, (meaning a composition before optional addition of any further ingredients) wherein at least 70% of the isolated material are nauplius stage I, more preferred at least 80%, even more preferred at least 90%, even more preferred at least 95%, and most preferred at least 99% of the isolated material are nauplius stage I in relation to the total weight or total number of organisms comprised in the product.

Furthermore, a preferred product according to the present invention for use as feed for initial life stages of aquatic animals such as marine fish larvae has a low amount of eggs. The reasoning for this is that barnacle eggs were found to be less digestible than nauplius larvae I in feeding tests carried out with marine fish larvae in the context of the present invention. Without being bound to any theory, it is assumed that particularly the egg shell/membrane is difficult to digest for a precocious marine fish. Therefore, it is preferred that a feed product, especially for use for marine fish larvae, according to the present invention has an amount of eggs which is less than 30%, more preferred less than 20%, even more preferred less than 10% and most preferred less than 5% in relation to the weight or number of organisms comprised in the product.

Furthermore, a preferred product according to the present invention for use as feed for initial life stages of aquatic animals such as marine fish larvae has a low amount of nauplius larvae of stage II. The outer form of the nauplius stage II, which has developed front horns and other appendages like the later nauplius stages may be less suitable as feed particles compared to the first stages without horn and other appendages.

In cases where the removed early live stages of barnacles are kept alive and incubated in water under suitable conditions (e.g. kept in sea water, and stored dark and cold) until processing takes place for a period of time after harvesting, the development of eggs and nauplius I larvae isolated from the cavity of the mature barnacles proceeds outside the parent. Thus, first-stage nauplii can potentially hatch from the eggs and the nauplius stage I further develop to nauplius stage II during such incubation. By incubating the animals for a defined time under suitable conditions it is thereby possible to influence the composition of the later preserved product in terms of amount of eggs and nauplii stage I or II. If desirable it is thus also possible to obtain a nutritional product with a high amount of stage II nauplii. As the preservation will stop the further development, it is possible to control the composition in accordance with the length of incubation after harvesting. In the context of the present invention, it was shown that harvested and fractionated nauplius stage I, which were incubated in sea water at 8° C., resulted in 92% amount of stage II after 12 hours of incubation.

In cases where there is a mixture of different nauplius stages and/or eggs, an optional separating step may be performed of the isolated eggs, nauplius stage I and nauplii of stage II in different size fractions by a mechanical separation method, preferably selected from sieving, filtration and/or centrifugation.

Alternatively, light may be used to separate nauplius larvae from eggs, as nauplius larvae from barnacles are known to be phototactic. Wave lengths in the range of 520 to 530 nm are found to be optimal in attracting cirriped nauplii of two different species, but other wave lengths were also found effective (Barnes, H.; Klepal, W. 1972. Phototaxis in stage I nauplius larvae of two cirripedes. J. Exp. Mar. Biol. And Ecol. Vol 10 (3), pp 267-273).

The described methods for harvesting have the great advantage that the obtained material is free from any other planktonic species. Harvesting methods including plankton catches of free-swimming organisms from the wild will always have other species of the same fraction and thus a non-pure product. By using the methods of the present invention, this can be avoided. Furthermore, it is possible to only obtain and harvest the earliest developmental stages of barnacles by these direct isolation methods from the mature barnacles.

II. Preservation of Barnacle Eggs, Nauplii Stage I and/or Nauplii Stage II

It is further preferred that the obtained isolated biological material comprising or substantially consisting of barnacle eggs and/or nauplii stage I, or in combination with nauplius stage II are preserved for further storage. The methods according to the present invention preferably include one or several methods chosen from cooling and/or freezing of the animals, heat treatment, use of a modified or controlled gas atmosphere, drying, irradiation, high pressure preservation and treatment with preserving chemicals. Preferably, several methods are combined with each other to obtain an optimal preservation and storage stability of the product. The applied method depends on the later use of the material, the requirements to its quality as well as the length of the time period for storage and the storage conditions in general.

Depending on the storage time cooling below room temperature is used, preferably at 4° C. or less. A preferred embodiment includes storage of the product below the freezing point of the animals, more preferably to a temperature of −18° C. or lower and most preferred to temperature of −80° C. or less. If particular stable storage is desired even liquid nitrogen can be used for storage. Freezing of the material below the freezing point, preferably at or below −80° C. directly or shortly after harvesting is a simple and effective method of preservation which results in a sufficient quality of the persevered material also after long-term storage of 6 months for many later applications. However, the storing stability of the product can be increased if the cooling/freezing is combined with other preservation methods. This is preferred if a very high quality and stability of the final product is afforded. Thus, in a preferred embodiment the biological material preserved by cooling is heat treated before cooling down or freezing. The cooling may also be combined with storage under a controlled or modified gas atmosphere.

Storage in a modified gas atmosphere preferably includes storage under a nitrogen atmosphere e.g. in a gastight container such as a plastic packaging. In a preferred embodiment the controlled atmosphere treatment is combined with a reduced temperature as described above. Alternatively, vacuum packing maybe used.

Preferred preservation methods comprising heat treatment can e.g. be heating of the material to less than 70° C., a pasteurization treatment by heat treatment at least 70-75° C., or sterilization by at least 100° C., preferably by 112° C. or more for a predefined period of time. The preferred method chosen will depend on the later use of the material as well as on the expected period of storage.

A particular preferred preservation method according to the present invention is pasteurization at a temperature of at least 70° C. for preferably at least 15 minutes, preferably at least 75° C. Thereafter, the material is preferably frozen and stored at −80° C. or lower. Tests have shown that high qualities of the obtained material are found if stored up to 6 months under these conditions. Advantages with the method are that all autolytic enzymes are destructed and vegetative stages of micro-organisms are killed which contributes to a more stable product. The process may be adapted in accordance with the type of produkt, pH, salt content, water content, protein content etc.

Another preferred method of preservation includes heating up the material to a temperature of less than 70° C. for at least 15 minutes, followed by freezing and subsequent storage at −80° C. or lower. Preferably, the temperature should be at least 55-60° C., preferably 60° C. or more, in order to deactivate most of the inherent enzymes. Tests have shown that high qualities of the obtained material are found if stored up to 6 months under these conditions. An advantage of the method is that the product becomes more stable against decomposition and autolysis. However, some groups of autolytic enzymes will still remain intact and not necessarily all vegetative stages of micro-organisms will be killed. The fact that at least some of the enzymes are still present, can be an advantage if used as feed for marine fish larvae in their initial life stages. These might require intact enzymes which come with the feed to be able to digest it.

Without being restricted to the following, typical examples for combined preservations methods and storage time according to the present invention are:

Semi-pasteurized by heating between 55 to less than 70° C. for at least 15 minutes, followed by freezing and subsequent storage at −80° C. or lower for up to six months.

Pasteurized at 70° C. or higher for 20 minutes and then frozen and stored at −80° C. or lower for up to six months.

Frozen and stored at −80° C. or lower for up to six months with or without preceding preservation. To further increase the storage stability, chosen temperatures for storage can even be lower. Preferably, the temperature used for storage can be −86° C. lower, more preferred −160° C. or lower, most preferred −196° C.

Pasteurized at a temperature of at least 70° C. for 20 minutes and then sterilized at 112° C. for 40 minutes, stored for up to 6 months at room temperature with air or N2 gas inside the packaging material.

The biological material, comprising or substantially comprising barnacle eggs and nauplii stage I may also be preserved by addition of preserving chemicals. Typically these chemicals can include sodium benzoate, potassium sorbate, sulfites etc. These are preferably added in low amounts to inhibit and/or stagnate the bacterial growth in the raw material.

Making the raw material alkaline, i.e. by adjusting to a pH of more than 9 by addition of an alkaline chemical, will prevent many bacteria species to develop into vegetative stages. Alternatively, acidifying of the material below pH 4.6 will also prevent most bacteria including *Clostridium botulinum* to develop from spores to vegetative stages.

The harvested biological material may also be persevered by drying, more preferred by freeze drying. Drying or freeze drying can be carried out directly or after one of the above described preservations methods.

III. Biochemical Composition

The eggs and nauplii of stage I are rich in highly unsaturated fatty acids, especially of DHA and EPA (see Tab 2 for a material which substantially consisted of nauplius stage I i.e. more than 90% by number of individs), which makes them suitable and beneficial for human and animal consumption.

The barnacle nauplii I comprise as much as ca. 70% phosphatidylcholine in their polar lipids. Phosphatidylcholine is recognized as beneficial for growth and survival of marine fish larvae.

In the present invention, it was surprisingly found that the eggs and nauplii stage I of barnacle also not being a natural feed for early life stages of fish and crustaceans are suitable as feed for these species.

In a preferred embodiment according to the present invention a lipid product such as an oil is extracted from a raw material mainly comprising eggs and/or nauplii of stage I. This lipid product may e.g. be used in applications where other marine oils such as from fish, krill, copepods or marine mammals are used today.

Composition after Preservation Treatment and Storage:

Barnacle nauplii stage I of *S. balanoides*, were harvested and thereafter treated by different methods for preserving and storage. After the preservation and storage the lipid composition was analysed. Lipids were extracted according to the method of Blight and Dyer 1959 (Blight, E. G. and Dyer, W. J. 1959. A rapid method of total lipid extraction and purification. Cand. J. Biochem. Physiol. 37: 911-917) and the total lipid content was analysed gravimetrically. The total amount of lipid related to the dry weight was in the range of 10-12%.

The lipid classes were analysed based on Reynold Homan, Maureen K. Anderson, Journal of Chrom. B. 708 (1998) 21-26 and Robert A. Moreau, Lipids, Vol. 41, no. 7 (2006). Quantitative analyses of fatty acids were performed according to AOCS Official Method Ce 1b-89.

The following experimental treatments were used for preservation and storage:

A) Pasteurized at 70° C. for 20 min and then frozen and stored at −80° C. for six months.

B) Frozen and stored at −80° C. for six months.

C) Pasteurized at 70° C. for 20 min and then sterilized at 112° C. for 40 min, stored for 6 months at room temperature with air inside the packaging material.

D) Pasteurized at 70° C. for 20 min and then sterilized at 112° C. for 40 min, stored for 6 months at room temperature with nitrogen gas inside the packaging material.

TABLE 1

Percentage polar and neutral lipids and fatty acids of S. balanoides nauplius 1 using different preserving methods; A) Pasteurized at 70° C. for 20 min and then frozen and stored at −80° C. for six months B) Frozen and stored at −80° C. for six months C) Pasteurized at 70° C. for 20 min and then sterilized at 112° C. for 40 min, stored for 6 months with air inside the packaging material at room temperature D) Pasteurized at 70° C. for 20 min and then sterilized at 112° C. for 40 min, stored for 6 months with nitrogen gas inside the packaging material at room temperature.

| | Preservation and storage method | | | |
|---|---|---|---|---|
| | A | B | C | D |
| % of total fat | | | | |
| Polar lipids | 71 | 52 | 71 | 66 |
| Neutral lipids | 29 | 48 | 29 | 34 |
| free fatty acids | 1 | 18 | 3 | 3 |
| % of total fatty acids (analysed in treatment A | | | | |
| DHA | 24 | | | |
| EPA | 27 | | | |
| Sum polyunsaturated fatty acids (n-3) | 53 | | | |

The percentage of polyunsaturated omega-3 fatty acids (n-3 fatty acids) was high in all analysed samples (Table 1), mainly due to a high content of docosahexaneoic acid (DHA, 22:6n-3) and eicosapentaenoic acid (EPA, 20:5n-3). These two fatty acids are recognized as particular important during the early development of marine animals, especially of marine fish larvae. But they are also found to be beneficial in development and nutrition of other animals including humans.

The preservation method affected the amount of neutral and polar lipids in the stored material. The preservation method without heat treatment (treatment B), only including freezing of the material, resulted in a reduced percentage of polar lipids and an increased amount of neutral lipids in relation to the total lipids. Furthermore, the amount of free fatty was increased, when only freezing was used. This may indicate a lipolytic activity in these samples, while heat sensitive enzymes such as the lipases seem to be heat inactivated in the other treatments. Although the heat treatment resulted in a more stable product during storage in terms of the lipid composition, only freezing may be used in applications where the obtained quality is sufficient for the targeted purpose since it resulted in a still acceptable composition even after storage for 6 months. Depending on the later application and required quality, freezing may therefore be used as an alternative and more simple method for preservation in comparison to the methods where freezing/chilling is combined with heat treatment.

TABLE 2

Fatty acid composition % of total fatty acids in nauplius 1 of S. balanoides of treatment A, analysed by the Norwegian test laboratory NOFIMA Biolab. PUFA are polyunsaturated fatty acids.

| Fatty acids | % of total fatty acids |
|---|---|
| 14:0 | 1.5 |
| 16:0 | 15.6 |
| 18:0 | 3.4 |
| 20:0 | <0.2 |
| 22:0 | <0.2 |
| 16:1 n-7 | 2.4 |
| 18:1 (n-9) + (n-7) + (n-5) | 15.1 |
| 20:1 (n-9) + (n-7) | 4.5 |
| 22:1 (n-11) + (n-9) + (n-7) | 1.1 |
| 24:1 n-9 | 0.2 |
| 16:2 n-4 | 0.2 |
| 16:3 n-4 | <0.2 |
| 18:2 n-6 | 0.8 |
| 18:3 n-6 | 0.2 |
| 20:2 n-6 | 0.6 |
| 20:3 n-6 | <0.2 |
| 20:4 n-6 | 1.1 |
| 22:4 n-6 | <0.2 |
| 18:3 n-3 | 0.4 |
| 18:4 n-3 | 0.9 |
| 20:3 n-3 | <0.2 |
| 20:4 n-3 | 0.2 |
| 20:5 n-3 | 27 |
| 21:5 n-3 | 0.4 |
| 22:5 n-3 | 0.2 |
| 22:6 n-6 | 24 |
| Sum saturated fatty acids | 20.5 |
| Sum monoene fatty acids | 23.4 |
| Sum PUFA (n-6) fatty acids | 2.6 |
| Sum PUFA (n-3) fatty acids | 53.3 |
| Sum PUFA fatty acids total | 56.1 |

IV. Feeding Trials Using Preserved Barnacle Nauplius I According to the Present Invention A feed mainly consisting of Barnacle nauplii stage I of *Semibalanus balanoides* was tested in semi-intensive and intensive cultivation experiments with marine fish and crustacean larvae. The preserved raw material used as feed was prepared as described above at the beginning of the detailed description section. The feed had a composition of at least 90% by number of individuals of nauplii I and between 0-10% of nauplii stage II.

Experiment 1: Trial on Common Sole, *Solea solea*

Larvae were divided into two experimental groups each of 500±10 individuals (three replicate tanks for each dietary group) at a concentration of 10 ind/L. The experimental groups were fed as follows:

Group A (control): fed a diet of enriched rotifers (6 ind/mL) from days 3-9 post hatching (ph), followed by a diet of rotifers (3 ind/mL) combined with Artemia nauplii (2 ind/mL, respectively) from days 9-12 and finally followed by a diet consisting solely of Artemia nauplii (4 ind/mL) from day 12 until the end of the experiment.

Group B: fed 50% rotifers (3 ind/mL) plus 50% Barnacle nauplii (3 ind/mL), previously preserved, from days 3-9, followed by 50% Artemia (3 ind/mL) plus 50% Barnacle nauplii (3 ind/mL) days 9-14.

Larval sampling was performed on days 6 ph (early rotifer phase), 9 ph (late rotifer phase), 12 ph (mixed rotifers/Artemia phase) and 14 ph (beginning of the Artemia phase).

Rotifers and Artemia nauplii were enriched with Algamac 3000 (Aquafauna Bio-Marine, Inc., Hawthorne, Calif., USA) using 0.5 g/million rotifers and 0.2 g/100,000 Artemia nauplii prior to feeding.

Figure 1:
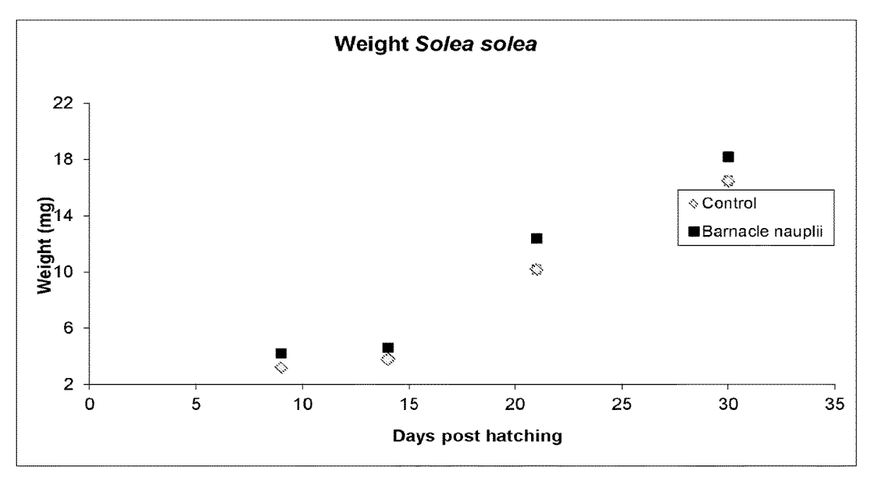
FIG. 1 shows the mean weight (±SD) of *Solea solea* larvae fed barnacles nauplii combined with traditional live feed used in traditional hatcheries (Group B) compared to the control (Group A) which only received the live feed diet.

The growth was higher in the group fed barnacle nauplii I than in the group fed the control diet (FIG. 1). The mean weight of fish larvae offered barnacle nauplii (Group B) was 21% higher than the control (Group A) on day 14, and the mean length of the larvae was 14% longer in Group B than in the control group. Survival was significantly higher in Group B (69%±2) compared to the control (65%±2). Additionally, malpigmented sole larvae were reduced from 5% in the control to 3% in the fish larvae that were offered nauplii I of S. balanoides.

Experiment 2: Trial on Shrimps, L. vannamei

A trial on shrimps was performed at a commercial hatchery, and compared with traditional live feed regimes commonly used which include live plankton, being Artemia nauplii. Barnacle nauplii I were offered as a substitute to Artemia nauplii (Group A). The control group received Artemia nauplii (Group B).

When the feeding trial was completed, the weight of shrimps in breeding tanks offered barnacle nauplii I (Group A) was 16% higher than in the control group without barnacles. This is due to both higher growth rate and survival of the shrimps.

Experiment 3. Commercial Trial on Senegalese Sole (Solea senegalensis)

A commercial trial with Senegalese sole was performed in 2.7 $m^3$ breeding tanks, using the S. balanoides nauplii I in one of the breeding tanks and conventionally enriched live Artemia nauplii I, as commonly used at commercial hatcheries, in several of the other breeding tanks. Fish larvae offered S. balanoides nauplii I had no malpigmentation, whereas 5% from the control tanks displayed such deformation. In addition, S. senegalensis offered S. balanoides nauplii stage I had a significantly more homogeneous size dispersion than those from the control.

Experiment 4. Feeding Trials with Atlantic Halibut, Atlantic Cod, and Ballan Wrasse Larvae Three industrial feeding trials were performed using the above mentioned preserved S. balanoides nauplius I in 5 to 6.6 $m^3$ breeding tanks containing Atlantic halibut, Atlantic cod and ballan wrasse larvae, respectively. The aim of the study was to observe sinking velocity of the diet being S. balanoides nauplia, and appetite of the fish larvae offered the new diet. After one hour, the surface water was sampled, and negligible sinking were observed in both breeding tanks. When sampled 4 hours after adding the diet, 25% of the S. balanoides nauplia were still in the upper water layer and available for fish larvae. 25 ballan wrasse larvae were sampled after one hour, and 3-20 S. balanoides nauplia were found in the gut except for two fishes that did not contain any food. The halibut larvae were directly observed in the breeding tanks, and they were actively feeding on the S. balanoides nauplia I. For the Atlantic cod, growth and survival was studied in addition to sinking rates. The commercial Atlantic cod nursery experienced 47% higher growth rate in terms of weight compared to the control which were fed enriched rotifers. These obtained survival rates were the highest ever achieved in this cod hatchery.

Using non-live feed diets as the one described here is always a challenge, because the sinking velocity is often too high, and the fish larvae show very little appetite on non-moving prey. In these three industrial trials, it is documented that this problem has been overcome by using the S. balanoides nauplii I as prey.

The experiments described showed high survival rates as well as good growth and larval quality when barnacles nauplii were used as a diet. Eggs and nauplii I of barnacles have typical sizes ranges from 100 to 500 μm, and do therefore cover the size spectre of todays live feed in marine aquaculture (rotifers 100-300 μm and Artemia nauplii typically between 350-800 μm).

The results of the start feeding experiments carried out indicate that the barnacle nauplii stage I are particular suitable as first feed for larvae/juveniles of aquatic animals in aquaculture. The material may also be used for ornamentals in general (ornamental vertebrates and invertebrates). By using them as feed or as a feed supplement many of the known problems in start feeding of fish larvae, especially of precocious marine fish larvae, can be overcome. The shown improved growth, larval quality, and survival rates clearly indicate this.

Other feeding trials where the material also included eggs and nauplius stage I which were not completely hatched yet, but still surrounded by the egg shell/membrane, indicated that these were not as suitable in start feeding of marine fish larvae as their digestibility in the gut seems to be limited. This may be due to the egg shell/membrane being more difficult to digest.

Furthermore, it is assumed that nauplius stage I are more suited for first feeding than nauplius stage II or even older nauplius stages as the later once have developed horns and other appendages which may reduce their ingestibility. It is likely that these horns/appendages could serve as a predator defense at least for marine fish larvae in the initial live stages. The horns in stage II nauplii may thus make them less attractive and suited as diet to the larvae compared to nauplii stage I.

The disclosed experimental results also indicate that a feed comprising nauplii stage I of barnacle or a material derived therefrom, can be used as a pharmaceutical composition i.e. a medicament, in particular for curing and/or preventing of mal developments as well as of diseases leading to reduced growth and higher mortalities. The obtained results disclosed in fish and shrimp cultivation clearly indicate that such a composition improves growth and survival of an animal such as a marine fish larva (experiment 1 and 3) or a crustacean (experiment 2). Furthermore, it demonstrates that the use of this composition resulted in a reduced malpigmentation in fish (experiment 1 and 3). Especially in the flatfish development of abnormalities like incomplete eye migration, mal pigmentation and skeletal deformations are major challenges, frequently observed and experienced in intensive production. A composition according to the present invention may be used to reduce these negative effects and abnormalities in early development.

The natural food for fish larvae of marine species such as cod, turbot and halibut consists typically and to a large extend of small species and young stages of marine copepods, which are present in coastal waters. Barnacle eggs and nauplii which are comprised inside the mature barnacles are not available for the fish larvae and do therefore not serve as a typical natural feed for early life stages of fish.

In general, all barnacles that brood eggs and nauplii I in the parent animal are of interest in the context of the present invention. One of the preferred applications of the described invention is the use as a first feed for larvae/juveniles of aquatic animals in aquaculture or for ornamentals in general.

Eggs and nauplii from barnacles can be used as food items/ingredients for fish larvae. The isolated biological material may, however, also be used for other feeding purposes such as for feeding for ornamental vertebrates (e.g. fish) and invertebrates or crustaceans.

A method for feeding of farmed aquatic animals and/or ornamental aquatic organisms preferably comprises the steps of preparation of a feed comprising nauplii of stage I as main ingredient and optionally other conventional feed ingredients. The feed may additionally comprise barnacle eggs and nauplius stage II from barnacle. Alternatively, nauplius stage I or a combination of nauplius stage I with eggs and/or stage II nauplius are used directly as a feed without further additives. In a preferred embodiment, the feeding of the isolated barnacle material (eggs/nauplii) especially for early live stages of fish and crustaceans is combined with feeding of other live feed such as rotifers or Artemia. The diet comprising nauplii I or a combination of nauplius stage I with eggs and/or nauplius stage II barnacles may also be used in combination with artificial diets such as micro diets, especially in the transitional period from live prey feeding to dry feed feeding. The material comprising nauplii I or a combination of nauplius stage I with eggs and/or nauplius stage II may be used as a partly or total replacement for live feed during start feeding of marine fish larvae.

In a preferred embodiment the nutritional product according to the present invention, especially the feed product, substantially only comprises barnacle material consisting of nauplii I or a combination of nauplius stage I with eggs and/or nauplius stage II of said barnacle.

In another preferred embodiment the nutritional product according to the invention substantially only consists of biological material derived from nauplii I or a combination of nauplius stage I with eggs and/or nauplius stage II of a barnacle and no other added ingredients.

A typical method for feeding of farmed aquatic animals and/or ornamental vertebrates or invertebrates (e.g. according to the present inventions comprises the following steps:

i.) preparation of a feed comprising nauplius stage I or a combination of nauplius stage I with eggs and/or nauplius stage II and other conventional feed ingredients; or ii.) using nauplii stage I or a combination of nauplius stage I with eggs and/or nauplius stage II directly as a feed without further additives, and iii.) adding the feed to the unit comprising the animal to be fed by manual feeding or by automatic feeding means.

The feed comprising barnacle nauplii stage I or a combination of nauplius stage I with eggs and/or nauplius stage II can thus be added to the unit comprising the animal to be fed by manual feeding or by automatic feeding means. Feeding can be carried out in a batch wise manner or continuously depending on the application. It may be added directly after harvesting or after preservation and optionally storage. If stored at low temperatures it may be added e.g. after thawing, partly thawing or in a frozen state.

In a preferred embodiment, the feed is used for a marine fish larvae such as a larvae of Atlantic cod, turbot, sea bass, sea bream, halibut.

In another preferred embodiment, the feed according to the present invention is used for farmed species of crustacean including species belonging to the group of prawns, lobster, shrimp, crabs etc.

Thus, a new feed for aquatic animals, especially of farmed aquatic animals in their early live stages has been invented in the present invention. In another preferred embodiment, the feed according to the present invention is used for ornamental vertebrates such as fish as well as invertebrates such as corrals, anemones, sea urchins.

Based on their biochemical composition other application such as for health products, human consumption, feed additives and supplements, medical products, functional feed are possible. There is a need for new and alternative sources for marine oils with a high content of omega-3 fatty acids. A material or oil derived/extracted from barnacle eggs and/or nauplii according to the invention can serve as such a new resource.

It will be appreciated that the features of the invention described in the foregoing can be modified without departing from the scope of the invention.

Definitions of Terms

Barnacle: By barnacle is meant a type of arthropod belonging to infraclass Cirripedia in the subphylum Crustacea.

Sessile barnacle: Non-motile barnacle attached to a surface.

Functional feed: By functional feed is meant a feed which provides other merits than just nutritional effects but also effects such as health effects, stimulation of the immune response, prevention of risk of diseases etc.

Pasteurization: By pasteurization is meant a process of heating a material whereby the spoilage of the treated material is slowed down by reducing the number of viable microorganisms and/or inhibiting the growth of microorganisms in the pasteurized product.

Sterilization: A process whereby all microbial life in the product are killed or eliminated, including transmissible agents such as fungi, bacteria, viruses, spores etc.

Preservation: By preservation of the biological material is meant a process of treating and handling of the material to stop or slow down spoilage (e.g. by microorganisms), loss of quality (e.g. by oxidation, rancidity), visual deterioration, inert enzyme activities etc.) and/or nutritional value and thus allow for longer food storage.

Nutritional product: By the term nutritional product is meant any nutritional product which can be used for/consumed by humans and/or animals, comprising products such as a feed, a health product, a feed supplement and/or a functional feed.

The invention claimed is:

1. A method of feeding a fish, a crab, a shrimp, a prawn, or a lobster, comprising:
   preparing a feed comprising eggs of a barnacle and/or nauplii of stage I of a barnacle; and
   adding the feed to a unit containing the fish, the crab, the shrimp, the prawn, or the lobster which results in the fish, the crab, the shrimp, the prawn, or the lobster being fed the feed comprising eggs of a barnacle and/or nauplii of stage I of a barnacle.

2. The method according to claim 1, wherein the feed further comprises nauplii of stage II of a barnacle.

3. The method according to claim 1, wherein the feed comprises living nauplii stage I of barnacles.

4. The method according to claim 1, wherein the fish is a fish larva.

5. The method according to claim 1, wherein the fish is a marine fish larva.

6. The method according to claim 1, wherein the feed comprises non-living developmental stages of barnacles.

7. The method according to claim 1, wherein the feed comprises preserved eggs or preserved nauplii stage I of barnacles.

* * * * *